(12) United States Patent
Chang et al.

(10) Patent No.: US 9,421,368 B2
(45) Date of Patent: Aug. 23, 2016

(54) DIABETES GLUCAGON MITIGATION SYSTEM AND METHOD WITH AN ELECTRICAL ENERGY WAVE GENERATOR

(71) Applicant: TAIWAN RESONANTWAVE INC., Taipei (TW)

(72) Inventors: Wen-Chieh Chang, Taichung (TW); Sophia Kao, Taichung (TW)

(73) Assignee: TAIWAN RESONANTWAVE INC., Taipei (TW)

( * ) Notice: Subject to any disclaimer, the term of this patent is extended or adjusted under 35 U.S.C. 154(b) by 57 days.

(21) Appl. No.: 14/529,189

(22) Filed: Oct. 31, 2014

(65) Prior Publication Data

US 2016/0121113 A1    May 5, 2016

(51) Int. Cl.
*A61N 1/00* (2006.01)
*A61N 1/36* (2006.01)
*A61N 1/372* (2006.01)

(52) U.S. Cl.
CPC ........ *A61N 1/36014* (2013.01); *A61N 1/37247* (2013.01)

(58) Field of Classification Search
CPC ........... A61N 1/36014; A61N 1/37247; A61N 1/36196; A61N 1/36189; A61N 1/36557; A61N 1/36121; A61N 1/36085
See application file for complete search history.

(56) References Cited

U.S. PATENT DOCUMENTS 5,231,988 A * 8/1993 Wernicke ........... A61N 1/36053
                                                         600/319
6,652,444 B1 * 11/2003 Ross ................... A61N 1/40
                                                         600/15

* cited by examiner

*Primary Examiner* — Mallika D Fairchild
(74) *Attorney, Agent, or Firm* — WPAT, P.C., Intellectual Property Attorneys; Anthony King

(57) ABSTRACT

A system and method for relieving high blood sugar factor of diabetes includes an electric energy wave generator with a frequency effect level control mode. The frequency effect level control mode includes a control of a single frequency effect period and a control of a multi-frequency modulation effect period and controls and emits a single frequency electric energy wave to a diabetic patient's body in the single frequency effect period according to the frequency effect level control mode and controls and emits a multi-frequency electric energy wave in a multi-frequency modulation effect period, so as to reduce and eliminate a high blood sugar factor of the diabetic patient's body by the electric energy wave.

9 Claims, 10 Drawing Sheets

DIABETES GLUCAGON MITIGATION SYSTEM AND METHOD WITH AN ELECTRICAL ENERGY WAVE GENERATOR

BACKGROUND OF THE INVENTION

1. Fields of the Invention

The present invention relates to a system and method for relieving high blood sugar factor of diabetes, and more particularly, to the electric energy wave formulation technology that uses frequency modulation to treat high blood sugar factor of diabetes.

2. Descriptions of Related Art

Diabetes is a serious metabolic disorder. If the secretion of insulin in a human body is insufficient, glucose will be unable to enter into cells or used by the cells, so that the glucose content in bood will be increased, and the metabolic disorder may occur. According to the standard set by American Diabetes Association, diabetes is diagnosed by meeting any one of the following conditions: 1) Fasting Plasma Glucose (FPG) is measured to be 7.0 Mmol/liter (126 mg/dl) or higher; 2) In the oral glucose tolerance test (OGTT), the plasma glucose is measured to be 11.1 Mmol/liter (200 mg/dl) or higher after orally taking 75 g of glucose for 2 hours; 3) In a random plasma glucose, the plasma glucose is measured to be 11.1 Mmol/liter (200 mg/dl) or higher, and the patient has high blood glucose symptoms; and 4) The glycated hemogoblin (HbAlC) is measured to be 6.5 or higher. If the level of human blood glucose is too high, glucose will be unable to be absorbed by kidney, so that the glucose will be discharged together with urine. If the urine contains a relatively large quantity of sugar, then diabetes will be developed. At present, there are two main methods used by Western medicine to treat diabetes: 1. Insulin Injection (Supplement insulin by injection), and Oral Medication (Control blood sugar by taking medicine orally). Although the aforementioned treatments can improve insulin secretion and lower insulin resistance to control the high blood sugar factor of a patient, yet these treatments can just control the blood sugar of diabetes only, but cannot cure diabetes. If a patient stops the insulin injection or oral medication, different complications of diabetes may occur. Furthermore, the aforementioned injection method is an invasive allopatic treatment, so that the patient's kidney may be injured easily after a long-term treatment, and ultimately the patient requires dialysis.

As to the treatment of diabetes by Chinese medicine, R.O.C. Pat. No. I356706 entitled "Chinese herb capable of controlling metabolic syndromes" has disclosed a composition of bidens and ginseng with the effects of promoting the secretion of insulin and reducing the resistance of insulin. Although the conventional treatment can regulate the value of human blood sugar, this treatment is still an oral medication treatment, so that it is generally considered as an indirect invasive treatment, and its potency has a chemical restriant effect on human body. Under the long-term oral medication treatment, the patient's kidney may be injured or damaged easily.

According to the theory of quantum medicine, all living things and life forms have their own physiological frequency (which is the biological resonant wave), and harmonized wave frequency occurs in healthy human bodies. On the other hand, a disordered wave frequency occurred in human body indicates functional degradation of the living thing and sickness caused by a harmonic interference of diseases or viruses. In 1930, American physicist, Royal Rife, discovered that every object contains bacteria and viruses having their own natural frequency, and such discovery was used by doctors of University of Southern California for medical tests in 1934 and satisfactory results were achieved. Royal Rife's research discovered that different resonant waves have different physiological reactions to human body. Thereafter, a Canadian corporation, Resonant Light Technology Inc. developed a resonant wave health instrument for measuring the physiological frequency of a human body. The electric energy wave emitted from the instrument has a wavelength of 4~20 microns (um), which is very close to the wavelength of the biological wave of a human body (3~45 um), so as to provide a healthcare function to human body. At present, researches on the subject of treating cancers by electromagnetic waves are conducted extensively. Although the prior art has introduced electric energy waves into human body to produce resonance with the physiological frequency of human body, so as to achieve the treatment effect, yet the conventional techniques or researches do not use the electric energy wave technology to create a frequency modulation treatment formulation for reducing or eliminating high blood sugar factor of diabetes to cure diabetes effectively.

Since the biological resonant waves probably have high efficacy in curing human diseases, and none of the prior art has applied the electric energy wave formulation to reduce or eliminate high blood sugar factor of diabetes, the inventor of the present invention conducted extensive researches and experiments, and finally designed an electric energy wave formulation for curing diabetes.

SUMMARY OF THE INVENTION

Therefore, it is a primary objective of the present invention to provide a system and method for relieving high blood sugar factor of diabetes, and the system and method primarily use electric energy waves of frequency modulation to reduce or eliminate a high blood sugar factor of diabetes, and clinical experiments show that the electric energy wave controlled and generated by frequency modulation can reduce or eliminate the high blood sugar factor of diabetes effectively and lower the level of glycated hemoglobin, so as to promote insulin secretion and lower insulin resistance. To achieve the aforementioned objective, the present invention provides a technical measure including a system with an electric energy wave generator, and the electric energy wave generator has a frequency effect level control mode set for controlling and generating electric energy waves. The frequency effect level control mode includes a control of at least one single frequency effect period and a control of at least one multi-frequency modulation effect period. The electric energy wave generator controls and emits a single frequency electric energy wave to a diabetic patient's body in the single frequency effect period according to the frequency effect level control mode and controls and emits a multi-frequency electric energy wave in the multi-frequency modulation effect period, so as to reduce or eliminate a high blood sugar factor (such as blood glucose and glycated hemoglobin) of the diabetic patient's body.

DETAILED DESCRIPTION OF THE PREFERRED EMBODIMENT

I. Basic Technical Characteristics of the Present Invention

Figure 1:
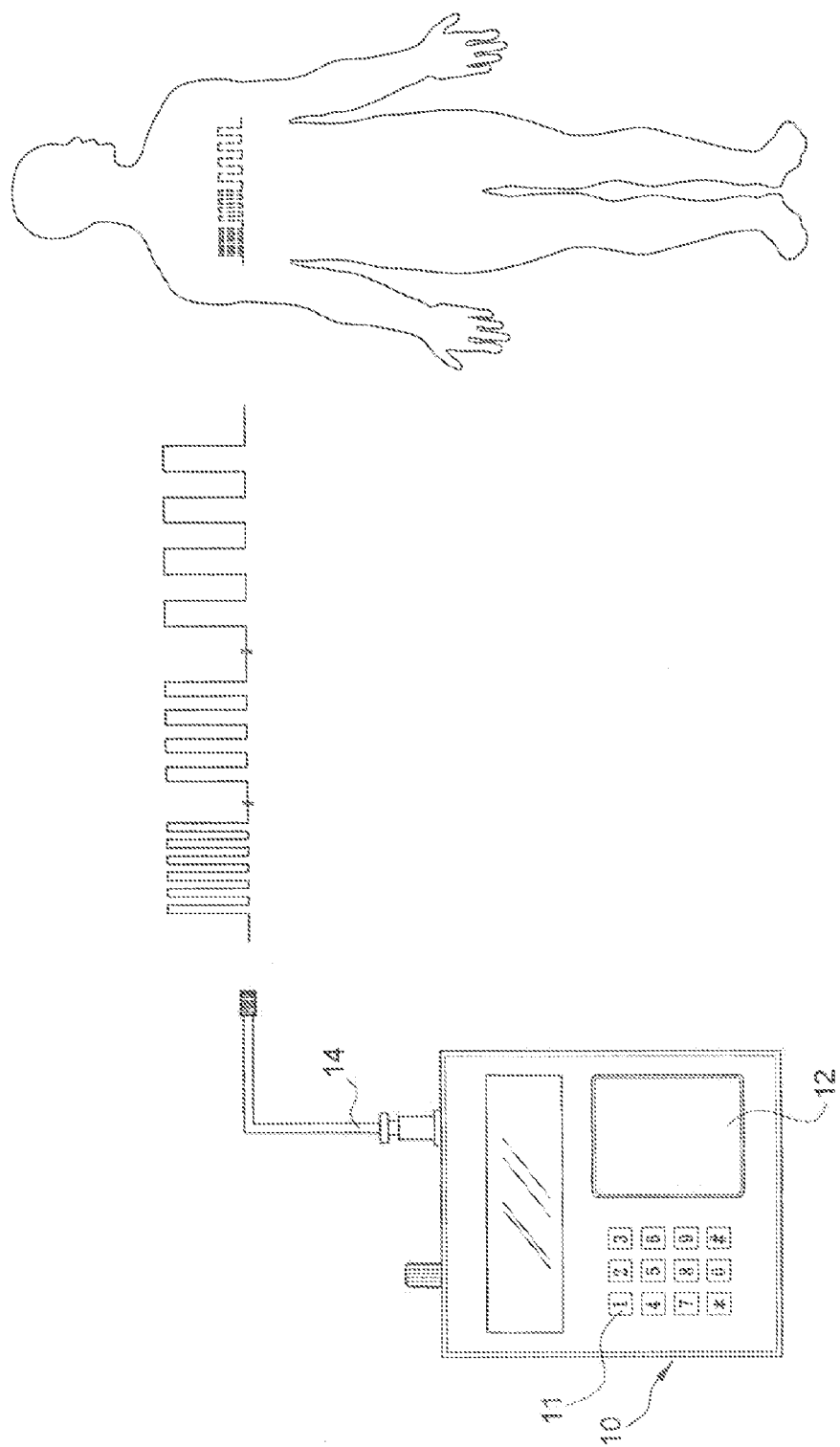
FIG. 1 is a schematic view of electric energy wave in a light energy form of a preferred embodiment of the present invention.
Figure 2:
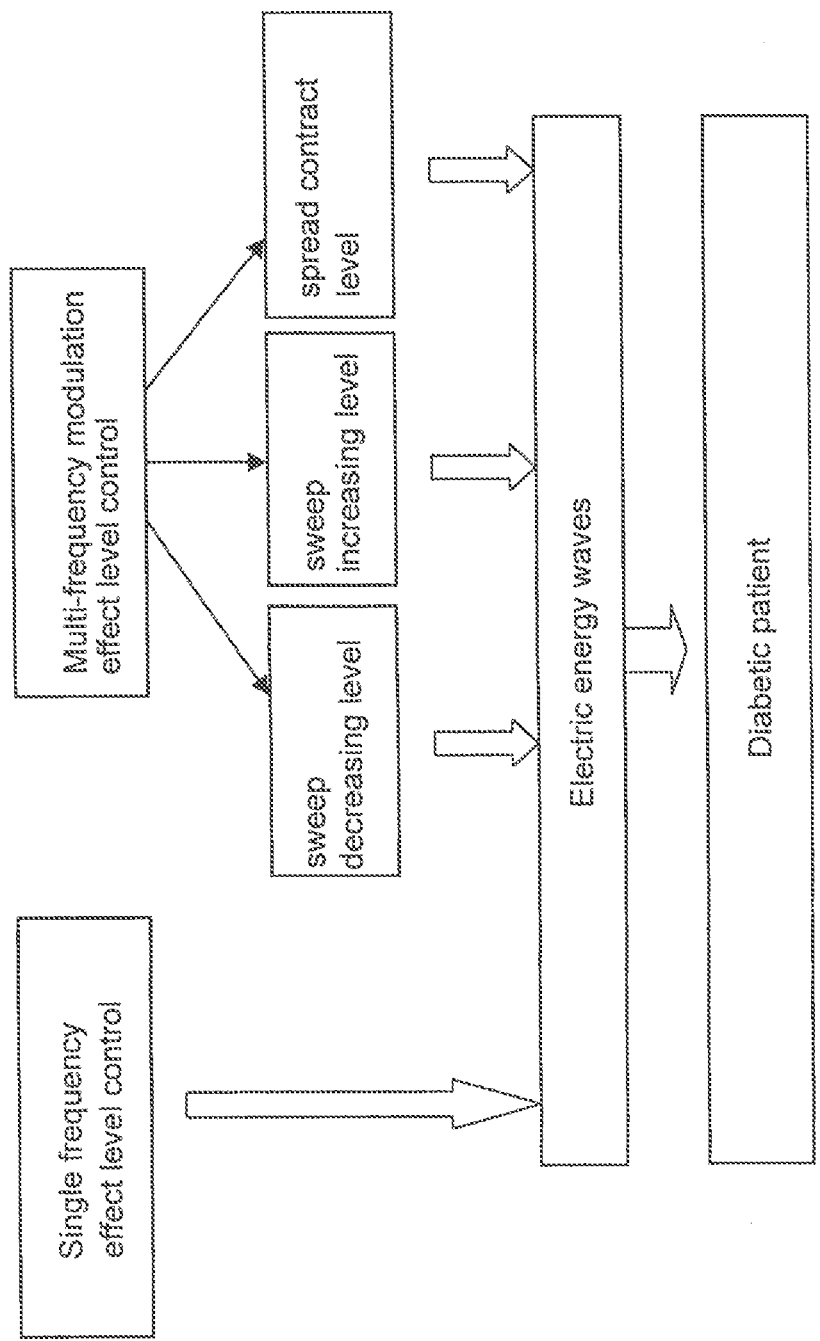
FIG. 2 is a schematic view of the architecture of a control formulation of a frequency effect period of the present invention.
Figure 3:
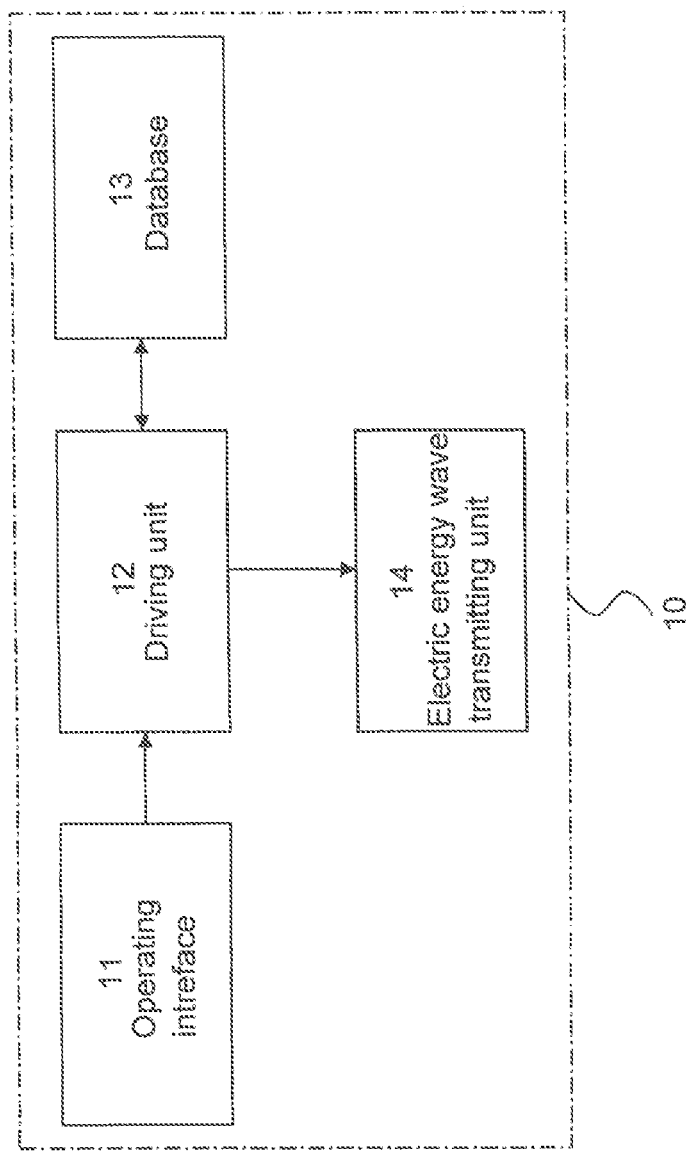
FIG. 3 is a schematic block diagram of the present invention.

Referring to FIGS. 1 to 3 for a system including an electric energy wave generator with the technical characteristics for achieve the objective of the present invention, the electric energy wave generator sets a frequency effect level control mode for controlling the generation of electric energy waves, and the electric energy wave generator 10 is used for emitting electric energy waves to a diabetic patient's body. The frequency effect level control mode includes the control of at least one single frequency effect period and the control of at least one multi-frequency modulation effect periods. The electric energy wave generator controls and emits a single frequency electric energy wave to a diabetic patient's body in the single frequency effect period according to the frequency effect level control mode and controls and emits a multi-frequency electric energy wave in the multi-frequency modulation effect period, so as to reduce or eliminate a high blood sugar factor (such as blood glucose and glycated hemoglobin) of the diabetic patient's body.

II. Preferred Embodiments of Controlling and Emitting an Electric Energy Wave in Accordance with the Present Invention To set the frequency effect level control mode of the electric energy wave and controlling and emitting the single frequency electric energy wave to a diabetic patient's body in the single frequency effect period and controlling and emitting the multi-frequency electric energy wave in the multi-frequency modulation effect period according to the frequency effect level control mode, the electric energy wave generator 10 of the system of the present invention as shown in FIGS. 1 and 3 comprises an operating interface 11, a controlling and driving unit 12, a database 13 for storing spectral data of the electric energy wave, and an electric energy wave transmitting unit 14. The operating interface 11 is operated by a user to turn on or off the electric energy wave generator 10. The controlling and driving unit 12 is triggered by the operating interface 11 to read the spectral data stored in the database 13 and output a driving instruction signal for controlling a connection or disconnection of the electric energy wave transmitting unit 14, so that the electric energy wave transmitting unit 14 emits the electric energy waves corresponsive to the spectral data. The electric energy wave transmitting unit 14 emits an electric energy wave to the patient's body in the level according to the driving instruction signal. In FIG. 1, the electric energy wave transmitting unit 14 is an emitter that emits an electromagnetic wave of a specific frequency to the outside. In addition, the electric energy wave transmitting unit 14 may be a light wave emitter that emits a light wave of a specific frequency, or a combination of an audio amplifier and loudspeaker that emits a sound wave of a specific frequency. It is noteworthy that the present invention an electric energy wave generator available in the market can be used as long as the electric energy wave generator can control the emission time of the electric energy wave and modulate the frequency in different periods, and such electric energy wave generator can used as a formulation for improving the high blood sugar factor of diabetes.

Figure 4:
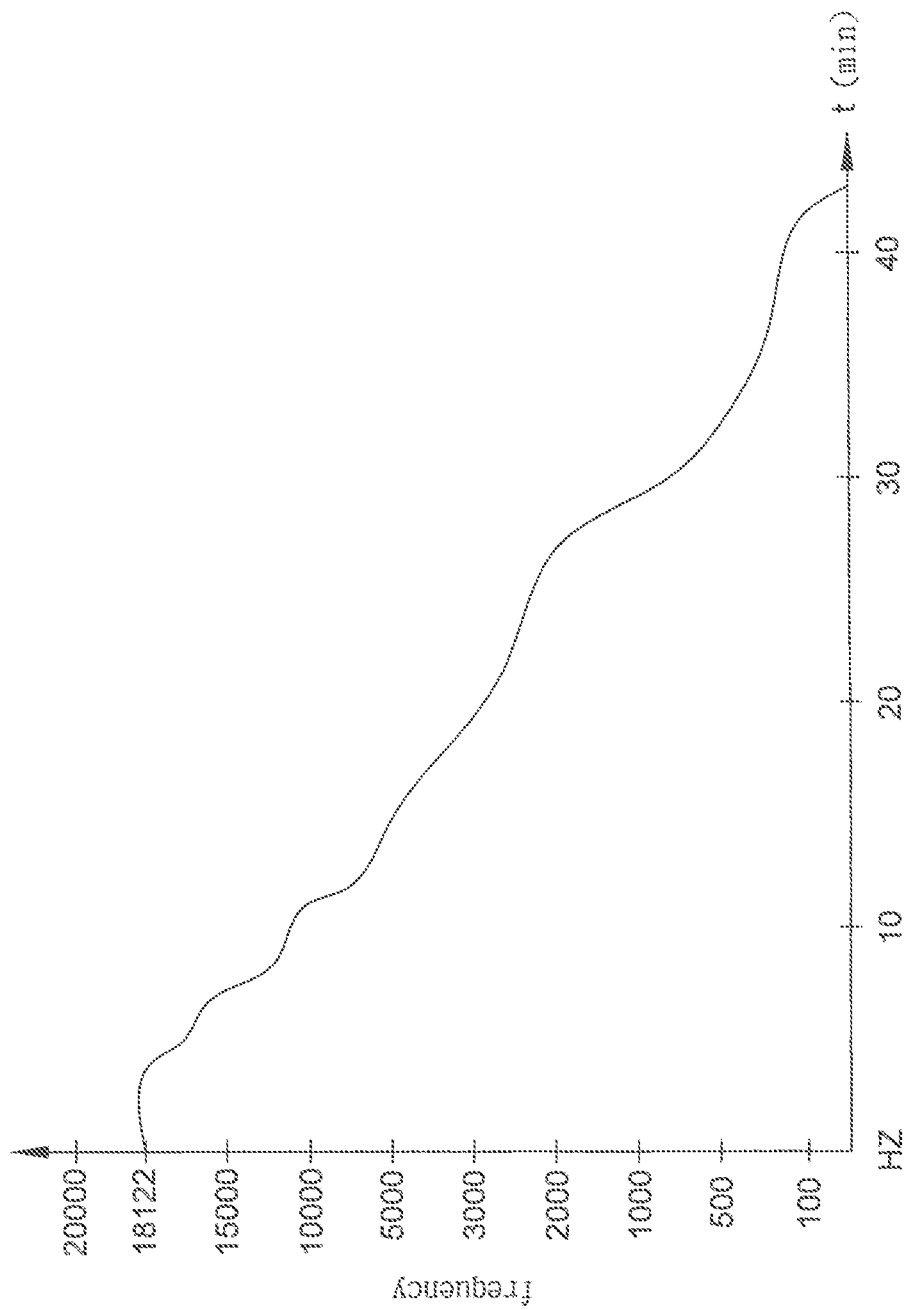
FIG. 4 is a graph showing a trend of an electric energy wave frequency modulation of the present invention.
Figure 5:
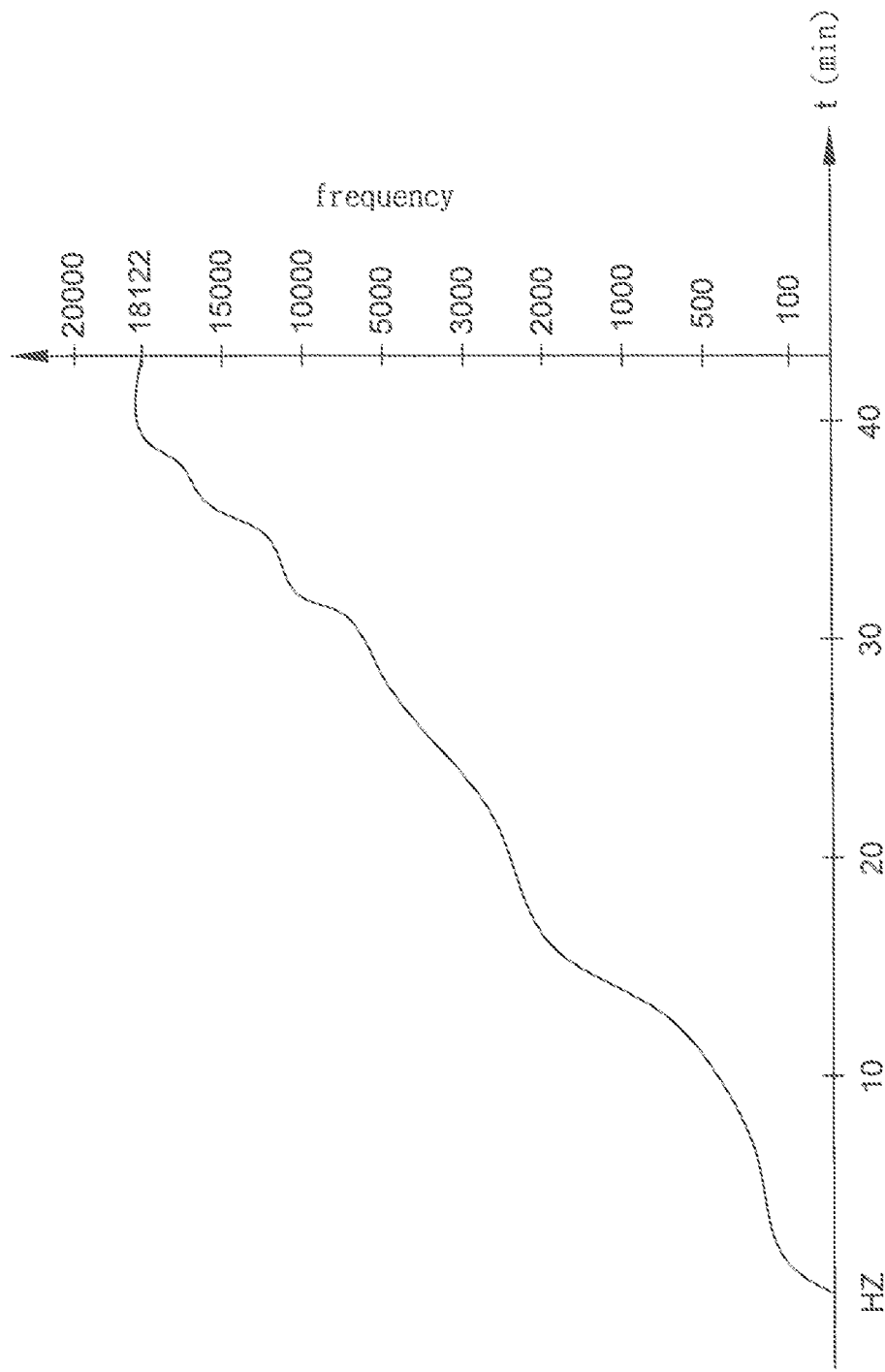
FIG. 5 is a graph showing another trend of an electric energy wave frequency modulation of the present invention.

III. Experiments of the Present Invention 3.1 Frequency Effect Level Control Mode of Electric Energy Wave of the Present Invention In an experiment of the present invention, the electric energy wave has a rectangular waveform, and the emittance of the electric energy wave in each duty cycle is 70% (in other words, 70% is the output of square waves with positive potential, and the remaining 30% is in an OFF state with zero potential). The time for the single frequency effect period and the multi-frequency modulation effect period are 42.39% and 57.61% of the whole effect periods respectively. There are a multiple of controls of the single frequency effect periods, and the frequency of electric energy wave controlled in each single frequency effect period is different. Under the basic principle of variable frequency mechanism of the frequency effect level control mode of the electric energy wave of the present invention, the frequency is decreasing (as shown in FIG. 4) or increasing (as shown in FIG. 5) from the start to the end of the whole effect period. In this experiment, the frequency is decreasing from the start to the end of the effect period. There are a multiple of controls of the multi-frequency modulation effect period, and the control is at least one selected from the group consisting of a control of the sweep decreasing effect period, a control of the sweep increasing effect period, and a control of the spread contract effect period, wherein the control of the sweep decreasing effect period controls the electric energy wave to have a frequency decreasing distribution in a predetermined bandwidth in the sweep decreasing effect period, and the control of the sweep increasing effect period controls the electric energy wave to have a frequency increasing distribution in a predetermined bandwidth in the sweep increasing effect period, and the control of the spread contract effect period controls the electric energy wave to have an alternate increasing frequency and decreasing frequency distribution in a predetermined bandwidth in the spread contract effect period. The sweep decreasing effect period, the sweep increasing effect period and the spread contract effect period in the multi-frequency modulation effect periods are 30.23%, 43.91% and 25.86% of the total time of the effect periods respectively. Every two adjacent frequency values controlled in the sweep decreasing effect period have a difference of 1 Hz. Every two adjacent frequency values controlled in the sweep increasing effect period have a difference of 1 Hz. Every two adjacent increasing frequency values and every two adjacent decreasing frequency values controlled in the spread contract effect period have a difference of 1 Hz. The predetermined bandwidth controlled in the sweep decreasing effect period is 3 Hz. The predetermined bandwidth controlled in the sweep increasing effect period is 9 Hz. The predetermined bandwidth controlled in the spread contract effect period is 9 Hz.

Figure 6:
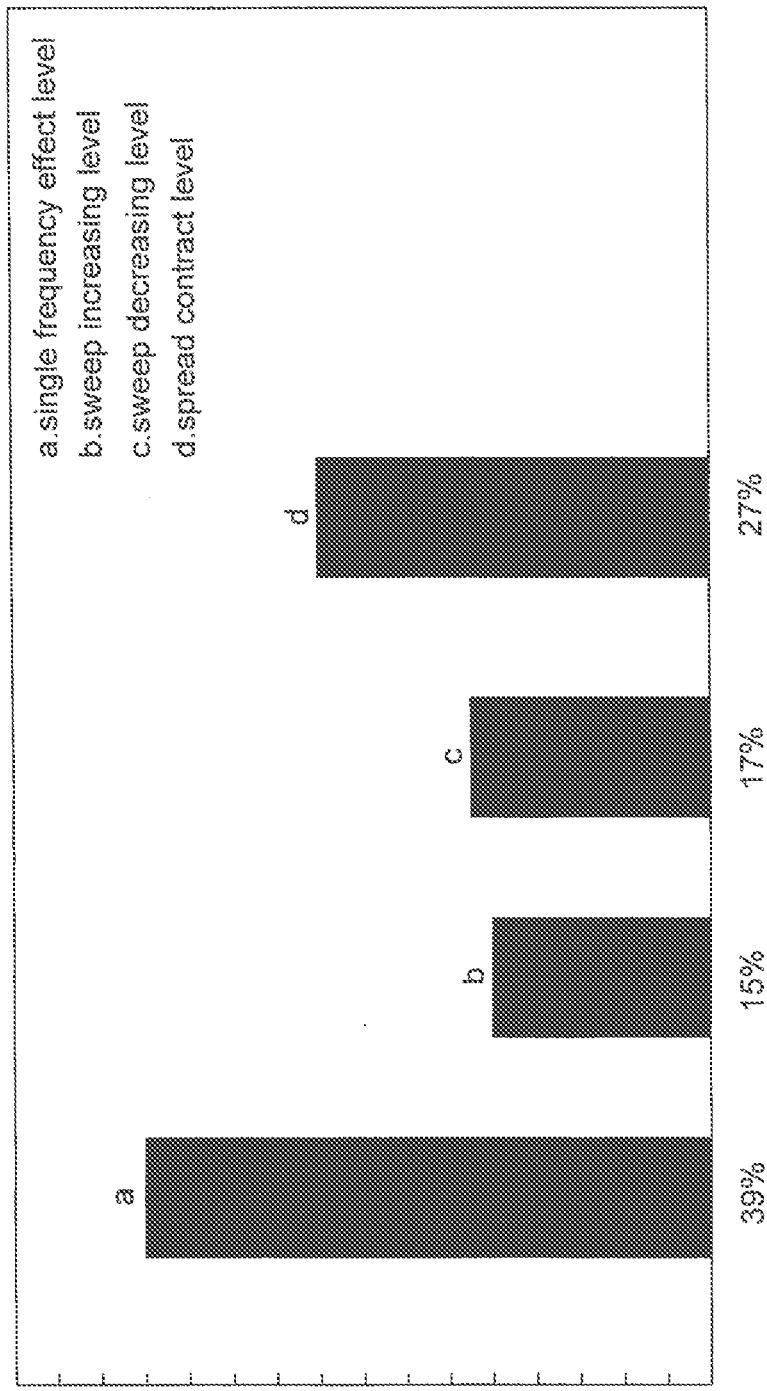
FIG. 6 is a schematic view showing the proportion of different frequency effect periods of the present invention.

In FIGS. 4 to 6 and Table 1, the control of the single frequency effect period of the present invention is represented by "Single Frequency", the control of the sweep decreasing period is represented by "Sweep Decreasing", the control of the sweep increasing period is represented by "Sweep Increasing", and the control of the spread contract period is represented by "Spread Contract".

TABLE 1

| Level | Waveform | Base | Width | # Freqs. | Time each | Total Time | Pulse | Rate | WaveShape | Duty Cycle | Output |
|---|---|---|---|---|---|---|---|---|---|---|---|
| 1 | Single Frequency | 18122,0 | | 1 | 0:07 | 00:00:07 | ON | 1 | Square | 70% | Positive |
| 2 | Single Frequency | 10000,0 | | 1 | 0:15 | 00:00:15 | ON | 1 | Square | 70% | Positive |
| 3 | Single Frequency | 7344,00 | | 1 | 0:19 | 00:00:19 | ON | 1 | Square | 70% | Positive |
| 4 | Single Frequency | 5000,00 | | 1 | 0:24 | 00:00:24 | ON | 1 | Square | 70% | Positive |
| 5 | Single Frequency | 4200,00 | | 1 | 0:26 | 00:00:26 | ON | 1 | Square | 70% | Positive |
| 6 | Single Frequency | 3672,00 | | 1 | 0:28 | 00:00:28 | ON | 1 | Square | 70% | Positive |
| 7 | Sweep Decreasing | 3175,00 | 2 | 3 | 0:10 | 00:00:30 | ON | 1 | Square | 70% | Positive |
| 8 | Single Frequency | 3000,00 | | 1 | 0:31 | 00:00:31 | ON | 1 | Square | 70% | Positive |
| 9 | Sweep Decreasing | 2127,00 | 1 | 2 | 0:18 | 00:00:36 | ON | 1 | Square | 70% | Positive |
| 10 | Single Frequency | 2112,00 | | 1 | 0:35 | 00:00:35 | ON | 1 | Square | 70% | Positive |
| 11 | Spread Contract . . . | 2007,00 | 7 | 15 | 0:02 | 00:00:30 | ON | 1 | Square | 70% | Positive |
| 12 | Single Frequency | 1865,00 | | 1 | 0:37 | 00:00:37 | ON | 1 | Square | 70% | Positive |
| 13 | Single Frequency | 1850,00 | | 1 | 0:37 | 00:00:37 | ON | 1 | Square | 70% | Positive |
| 14 | Single Frequency | 1550,00 | | 1 | 0:39 | 00:00:39 | ON | 1 | Square | 70% | Positive |
| 15 | Single Frequency | 1234,00 | | 1 | 0:42 | 00:00:42 | ON | 1 | Square | 70% | Positive |
| 16 | Single Frequency | 1043,00 | | 1 | 0:44 | 00:00:44 | ON | 1 | Square | 70% | Positive |
| 17 | Single Frequency | 1000,00 | | 1 | 0:45 | 00:00:45 | ON | 1 | Square | 70% | Positive |
| 18 | Sweep Increasing | 921,000 | 2 | 3 | 0:15 | 00:00:45 | ON | 1 | Square | 70% | Positive |
| 19 | Single Frequency | 880,000 | | 1 | 0:47 | 00:00:47 | ON | 1 | Square | 70% | Positive |
| 20 | Sweep Decreasing | 867,000 | 1 | 2 | 0:23 | 00:00:46 | ON | 1 | Square | 70% | Positive |
| 21 | Spread Contract . . . | 807,000 | 7 | 15 | 0:03 | 00:00:45 | ON | 1 | Square | 70% | Positive |
| 22 | Spread Contract . . . | 778,000 | 9 | 19 | 0:03 | 00:00:57 | ON | 1 | Square | 70% | Positive |
| 23 | Single Frequency | 751,000 | | 1 | 0:49 | 00:00:49 | ON | 1 | Square | 70% | Positive |
| 24 | Spread Contract . . . | 730,000 | 7 | 15 | 0:03 | 00:00:45 | ON | 1 | Square | 70% | Positive |
| 25 | Sweep Decreasing | 705,000 | 3 | 4 | 0:12 | 00:00:48 | ON | 1 | Square | 70% | Positive |
| 26 | Sweep Increasing | 668,000 | 8 | 9 | 0:06 | 00:00:54 | ON | 1 | Square | 70% | Positive |
| 27 | Spread Contract . . . | 652,000 | 5 | 11 | 0:05 | 00:00:55 | ON | 1 | Square | 70% | Positive |
| 28 | Sweep Decreasing | 625,000 | 5 | 6 | 0:09 | 00:00:54 | ON | 1 | Square | 70% | Positive |
| 29 | Single Frequency | 612,000 | | 1 | 0:51 | 00:00:51 | ON | 1 | Square | 70% | Positive |
| 30 | Sweep Increasing | 595,000 | 5 | 6 | 0:09 | 00:00:54 | ON | 1 | Square | 70% | Positive |
| 31 | Spread Contract . . . | 542,000 | 9 | 19 | 0:03 | 00:00:57 | ON | 1 | Square | 70% | Positive |
| 32 | Single Frequency | 522,000 | | 1 | 0:53 | 00:00:53 | ON | 1 | Square | 70% | Positive |
| 33 | Sweep Increasing | 484,000 | 4 | 5 | 0:11 | 00:00:55 | ON | 1 | Square | 70% | Positive |
| 34 | Sweep Decreasing | 462,000 | 3 | 4 | 0:14 | 00:00:56 | ON | 1 | Square | 70% | Positive |
| 35 | Sweep Increasing | 435,000 | 9 | 10 | 0:06 | 00:01:00 | ON | 1 | Square | 70% | Positive |
| 36 | Sweep Decreasing | 421,000 | 3 | 4 | 0:14 | 00:00:56 | ON | 1 | Square | 70% | Positive |
| 37 | Sweep Increasing | 380,000 | 4 | 5 | 0:12 | 00:01:00 | ON | 1 | Square | 70% | Positive |
| 38 | Spread Contract . . . | 348,000 | 5 | 11 | 0:05 | 00:00:55 | ON | 1 | Square | 70% | Positive |
| 39 | Sweep Decreasing | 302,000 | 2 | 3 | 0:20 | 00:01:00 | ON | 1 | Square | 70% | Positive |
| 40 | Sweep Increasing | 160,000 | 2 | 3 | 0:23 | 00:01:09 | ON | 1 | Square | 70% | Positive |
| 41 | Spread Contract . . . | 141,000 | 6 | 13 | 0:05 | 00:01:05 | ON | 1 | Square | 70% | Positive |
| 42 | Single Frequency | 125,000 | | 1 | 1:12 | 00:01:12 | ON | 1 | Square | 70% | Positive |
| 43 | Single Frequency | 095,000 | | 1 | 1:16 | 00:01:16 | ON | 1 | Square | 70% | Positive |
| 44 | Sweep Decreasing | 080,000 | 1 | 2 | 0:39 | 00:01:18 | ON | 1 | Square | 70% | Positive |
| 45 | Spread Contract . . . | 066,000 | 7 | 15 | 0:05 | 00:01:15 | ON | 1 | Square | 70% | Positive |
| 46 | Spread Contract . . . | 040,000 | 8 | 17 | 0:05 | 00:01:25 | ON | 1 | Square | 70% | Positive |
| 47 | Spread Contract . . . | 013,000 | 7 | 15 | 0:07 | 00:01:45 | ON | 1 | Square | 70% | Positive |
| 48 | Single Frequency | 009,390 | | 1 | 1:46 | 00:01:46 | ON | 1 | Square | 70% | Positive |
| 49 | Single Frequency | 006,300 | | 1 | 1:50 | 00:01:50 | ON | 1 | Square | 70% | Positive |
| 50 | Single Frequency | 001,200 | | 1 | 2:13 | 00:02:13 | ON | 1 | Square | 70% | Positive |

In the control of the sweep decreasing effect period, a different base frequency (Base) and a different bandwidth (Width) are set for different periods in a first frequency range, the first output frequency in the first frequency range is the sum of the bandwidth and the base frequency, and the second output frequency is equal to the first output frequency minus an adjusting factor (such as 1 Hz). If the next output frequency is equal to the base frequency, the next frequency is the last output frequency. For example, if the base frequency is equal to 100 Hz, the bandwidth (Width) is equal to 3 Hz, and the emission time of each frequency at such period is equal to 3 seconds, the number of frequencies (freqs) will be equal to 4 according to the aforementioned formula and the frequencies of 103 Hz, 102 Hz, 101 Hz and 100 Hz are outputted sequentially, and the total emission time at such period is accumulated to be 3*(3+1)=12 seconds.

In the control of the sweep increasing period, a different base frequency (Base) and a different bandwidth (Width) are set for different periods in the second frequency range, and the first output frequency in the second frequency range is equal to the base frequency, and the second output frequency is equal to the first output frequency plus an adjusting factor (such as 1 Hz). If the next output frequency is equal to the sum of the base frequency and the bandwidth, the next frequency will be the last output frequency. For example, if the base frequency is equal to 100 Hz, the bandwidth is equal to 3 Hz, and the emission time of each frequency at such period is equal to 3 seconds, the number of frequencies will be equal to 4 according to the aforementioned formula, and the frequencies of 100 Hz, 101 Hz, 102 Hz and 103 Hz are outputted sequentially, and the total number of the emission time at such period is accumulated to be 3*(3+1)=12 seconds.

In the control of the spread contract, a base frequency (Base) and a different bandwidth (Width) are set for different period in the third frequency range, and the first output frequency of the third frequency range is the sum of the bandwidth and the base frequency, and the second output frequency is equal to the bandwidth minus the base frequency, and then an adjusting factor (such as 1 Hz) is subtracted from the first frequency to obtain the third output frequency, and then an adjusting factor is subtracted from the second frequency to obtain the fourth output frequency. If the next frequency is equal to the base frequency, then the frequency will be the last output frequency. For example, if the base frequency is equal to 100 Hz, the bandwidth is equal to 3 Hz, and the emission time of different frequencies of such period is equal to 3 seconds, the number of frequencies will be 7, and the frequencies of 103 Hz, 97 Hz, 102 Hz, 98 Hz, 101 Hz, 99 Hz and 100 Hz are outputted sequentially, and the total emission time of such period is accumulated to be 3*(2*3+1)=21 seconds.

In Table 1, the bandwidth controlled in the sweep decreasing effect period falls within a range of 1~3 Hz, and the number of output frequencies falls within a range of 2~4. The bandwidth controlled in the sweep increasing period falls within a range of 2~9 Hz, and the number of output frequencies falls within a range of 3~10. The bandwidth controlled in the spread contract period falls within a range of 5~9 Hz, and the number of output frequencies falls within a range of 11~19.

3.2. Operation of the Experiment of the Present Invention

Clinical experiments show that the best time of curing diabetes by the present invention is 60 minutes after the last meal of each day. The effect time (which is the treatment time) is approximately equal to 44 minutes and 21 seconds for each time and divided into 50 periods. In these 50 periods, the waveforms of the electric energy waves are square waves with positive potential, and the emittance of the square wave with positive potential in each duty cycle is approximately equal to 70%. In other words, the waveform of the base frequency includes a high voltage of the positive potential in 70% of the time, and a zero voltage (or negative potential) in the remaining 30% of the time, or it is defined that a frequency (ON) is transmitted in 70% of the time, and no frequency (OFF) is transmitted in 30% of the time within pulse rate cycle (for transmitting an ON/OFF cycle of the frequency, and the Pulse Rate as shown in Table 1 is equal to 1 Hz. A course is conducted continuously for approximately 20~40 days to obtain preliminary improvement. In FIG. 1, the electric energy wave generator 10 is turned on when a diabetic patient wants to have the electric energy wave treatment, and the electric energy wave transmitting unit 14 is driven by the driving instruction signal to emit an electric energy wave according to the frequency effect level control mode of the electric energy wave.

In FIG. 4 and Table 1, the frequency is equal to 18122 Hz measured at the beginning of the effect period in an experiment of the present invention, and the frequency drops gradually to the final 1.2 Hz. Table 1 shows that there are six single frequency effect periods at first. In other words, the frequency of the electric energy wave at the $1^{st}$ to the $6^{th}$ period is a single frequency controlled in the single frequency effect period, and the frequencies of different periods are different and are decreased progressively. In the figure and table, the frequency drops from 18122 Hz to 3672 Hz sequentially in different periods, and the time of the single frequency effect period is equal to 7 seconds, 15 seconds, 19 seconds, 24 seconds, 26 seconds and 28 seconds. The electric energy wave at the $7^{th}$ period has a frequency in a sweep decreasing form controlled in the sweep decreasing effect period, a base frequency equal to 3175 Hz, a bandwidth equal to 2 Hz, and a number of frequencies equal to 3, and a treatment time of 10 seconds*3=30 seconds. The electric energy wave at the $8^{th}$ period has a frequency in a single frequency form controlled in the single frequency effect effect period and equal to 300 Hz, and a treatment time equal to 31 seconds. The electric energy wave at the $9^{th}$ period has a frequency in a sweep decreasing form controlled in the sweep decreasing effect period, a base frequency of 2127 Hz, a bandwidth of 1 Hz, and a number of frequencies equal to 2, and a treatment time of 18 seconds*2=36 seconds. The electric energy wave at the $10^{th}$ period has a frequency in a single frequency form controlled in the single frequency effect period and equal to 2112 Hz and a treatment time of 35 seconds. The electric energy wave at the $11^{th}$ period has a frequency in a spread contract form controlled in the spread contract effect period, a base frequency of 2007 Hz, a bandwidth of 7 Hz, a number of frequencies equal to 15, and a treatment time of 2 seconds*15=30 seconds. The electric energy wave at the $12^{th}$~$17^{th}$ period has a frequency in a single frequency form controlled in the single frequency effect period and dropping from 1865 Hz to 1000 Hz progressively and a treatment time equal to 37 seconds, 37 seconds, 39 seconds, 42 seconds, 44 seconds and 45 seconds. The electric energy wave at the $18^{th}$ period has a frequency in a sweep increasing form controlled in the sweep increasing effect period level, a base frequency of 921 Hz, a bandwidth of 2 Hz, a number of frequencies equal to 3, and a treatment time of 15 seconds*3=45 seconds. The electric energy wave at the $19^{th}$ period has a frequency in a single frequency form controlled in the single frequency effect period and equal to 880 Hz, and a treatment time of 47 seconds. The electric energy wave at the $20^{th}$ period has a frequency in a sweep decreasing form controlled in the sweep decreasing effect period, a base frequency of 867 Hz, a bandwidth of 1 Hz, a number of frequencies equal to 2, and a treatment time of 23 seconds*2=46 seconds. The electric energy wave at the $21^{st}$ period has a frequency in a spread contract form controlled in the spread contract effect period, a base frequency of 807 Hz, a bandwidth of 7 Hz, a number of frequencies equal to 15, and a treatment time of 3 seconds*15=45 seconds. The electric energy wave at the $22^{nd}$ period has a frequency in a spread contract form controlled in the spread contract effect period, a base frequency of 778 Hz, a bandwidth of 9 Hz, a number of frequencies equal to 19, and a treatment time of 3 seconds*19=57 seconds. The electric energy wave at the $23^{rd}$ period has a frequency in a single frequency form controlled in the single frequency effect period and equal to 751 Hz, and a treatment time of 49 seconds. The electric energy wave at the $24^{th}$ period has a frequency in a spread contract form controlled in the spread contract effect period, a base frequency of 730 Hz, a bandwidth of 7 Hz, a number of frequencies equal to 15, and a treatment time of 3 seconds*15=45 seconds. The electric energy wave at the $25^{th}$ period has a frequency in a sweep decreasing form controlled in the sweep decreasing effect period, a base frequency of 705 Hz, a bandwidth of 3 Hz, a number of frequencies equal to 4, and a treatment time of 12 seconds*4=48 seconds. The electric energy wave at the $26^{th}$ period has a frequency in a sweep increasing form controlled in the sweep increasing effect period, a base frequency of 7668 Hz, a bandwidth of 8 Hz, a number of frequencies equal to 9, and a treatment time of 6 seconds*9=54 seconds. The electric energy wave at the $27^{th}$ period has a frequency in a spread contract form controlled in the spread contract effect period, a base frequency of 652 Hz, a bandwidth of 5 Hz, a number of frequencies equal to 11, and a treatment time of 5 seconds*11=55 seconds. The electric energy wave at the $28^{th}$ period has a frequency in a sweep decreasing form controlled in the sweep decreasing effect period, a base frequency of 625 Hz, a bandwidth of 5 Hz, a number of frequencies equal to 6, and a treatment time of 9 seconds and 54 seconds. The electric energy wave at the $29^{th}$ period has a frequency in a single frequency formed controlled in the single frequency effect period and equal to 612 Hz, and a treatment time of 51 seconds. The electric energy wave at the 30$^{th}$ period has a frequency in a sweep increasing form controlled in the sweep increasing effect period, a base frequency of 595 Hz, a bandwidth of 5 Hz, a number of frequencies equal to 6, and a treatment time of 9 seconds*6=54 seconds. The electric energy wave at the 31$^{st}$ period has a frequency in a spread contract form controlled in the spread contract effect period, a base frequency of 542 Hz, a bandwidth of 9 Hz, a number of frequencies equal to 19, and a treatment time of 3*19 seconds=57 seconds. The electric energy wave at the 32$^{nd}$ period has a frequency in a single frequency form controlled in the single frequency effect period and equal to 522 Hz, and a treatment time of 53 seconds. The electric energy wave at the 33$^{rd}$ period has a frequency in a sweep increasing form controlled in the sweep increasing effect period, a base frequency of 484 Hz, a bandwidth of 4 Hz, a number of frequencies equal to 5, and a treatment time of 11 seconds*5=55 seconds. The electric energy wave at the 34$^{th}$ period has a frequency in a sweep decreasing form controlled in the sweep decreasing effect period, a base frequency of 462 Hz, a bandwidth of 3 Hz, a number of frequencies equal to 4, and a treatment time of 14 seconds*4=56 seconds. The electric energy wave at the 35$^{th}$ period has a frequency in a sweep increasing form controlled in the sweep increasing effect period, a base frequency of 435 Hz, a bandwidth of 9 Hz, a number of frequencies equal to 10, and a treatment time of 6 seconds*10=60 seconds. The electric energy wave at the 36$^{th}$ period has a frequency in a sweep decreasing form controlled in the sweep decreasing effect period, a base frequency of 421 Hz, a bandwidth of 3 Hz, a number of frequencies equal to 4, and a treatment time of 14 seconds*4=56 seconds. The electric energy wave at the 37$^{th}$ period has a frequency in a sweep increasing form controlled in the sweep increasing effect period, a base frequency of 380 Hz, a bandwidth of 4 Hz, a number frequencies equal to 5, and a treatment time of 12 seconds*5=60 seconds. The electric energy wave at the 38$^{th}$ period has a frequency in a spread contract form controlled in the spread contract effect period, a base frequency of 348 Hz, a bandwidth of 5 Hz, a number of frequencies equal to 11, and a treatment time of 5 seconds*11=55 seconds. The electric energy wave at the 39$^{th}$ period has a frequency in a sweep decreasing formed controlled in the sweep decreasing effect period, a base frequency of 302 Hz, bandwidth of 2 Hz, a number of frequencies equal to 3, and a treatment time of 20 seconds*3=60 seconds. The electric energy wave at the 40$^{th}$ period has a frequency in a sweep increasing form controlled in the sweep increasing effect period, a base frequency of 160 Hz, a bandwidth of 2 Hz, a number of frequencies equal to 3, and a treatment time of 23 seconds*3=69 seconds. The electric energy wave at the 41$^{st}$ period has a frequency in a spread contract form controlled in the spread contract effect period, a base frequency of 141 Hz, a bandwidth of 6 Hz, a number of frequencies equal to 13, and a treatment time of 5 seconds*13=65 seconds. The electric energy waves at the 42$^{nd}$ and 43$^{rd}$ periods have a frequency in a single frequency form controlled in the single frequency effect period and dropping from 125 Hz to 95 Hz progressively, and a treatment time of 72 seconds and 76 seconds. The electric energy wave at the 44$^{th}$ period has a frequency in a sweep decreasing form controlled in the sweep decreasing effect period, a base frequency of 80 Hz, a bandwidth of 1 Hz, a number of frequencies equal to 2, and a treatment time of 39 seconds*2=78 seconds. The electric energy wave at the 45$^{th}$ period has a frequency in a spread contract form controlled in the spread contract effect period, a base frequency of 66 Hz, a bandwidth of 7 Hz, a number of frequencies equal to 15, and a treatment time of 5 seconds*15=75 seconds. The electric energy wave at the 46$^{th}$ period has a frequency in a spread contract form controlled in the spread contract effect period, a base frequency of 40z, a bandwidth of 8 Hz, a number of frequencies equal to 17, and a treatment time of 5 seconds*17=85 seconds. The electric energy wave at the 47$^{th}$ period has a frequency in a spread contract form controlled in the spread contract effect period, a base frequency of 13 Hz, a bandwidth of 7 Hz, a number of frequencies equal to 15, and a treatment time of 7 seconds*15=105 seconds. The electric energy waves at the 48$^{th}$ to 50$^{th}$ periods have a frequency in a single frequency form controlled in the single frequency effect period and dropping from 9 Hz to 1.2 Hz progressively, and a treatment time of 106 seconds, 110 seconds and 133 seconds.

3.3. Experiment Results of the Present Invention

Figure 7:
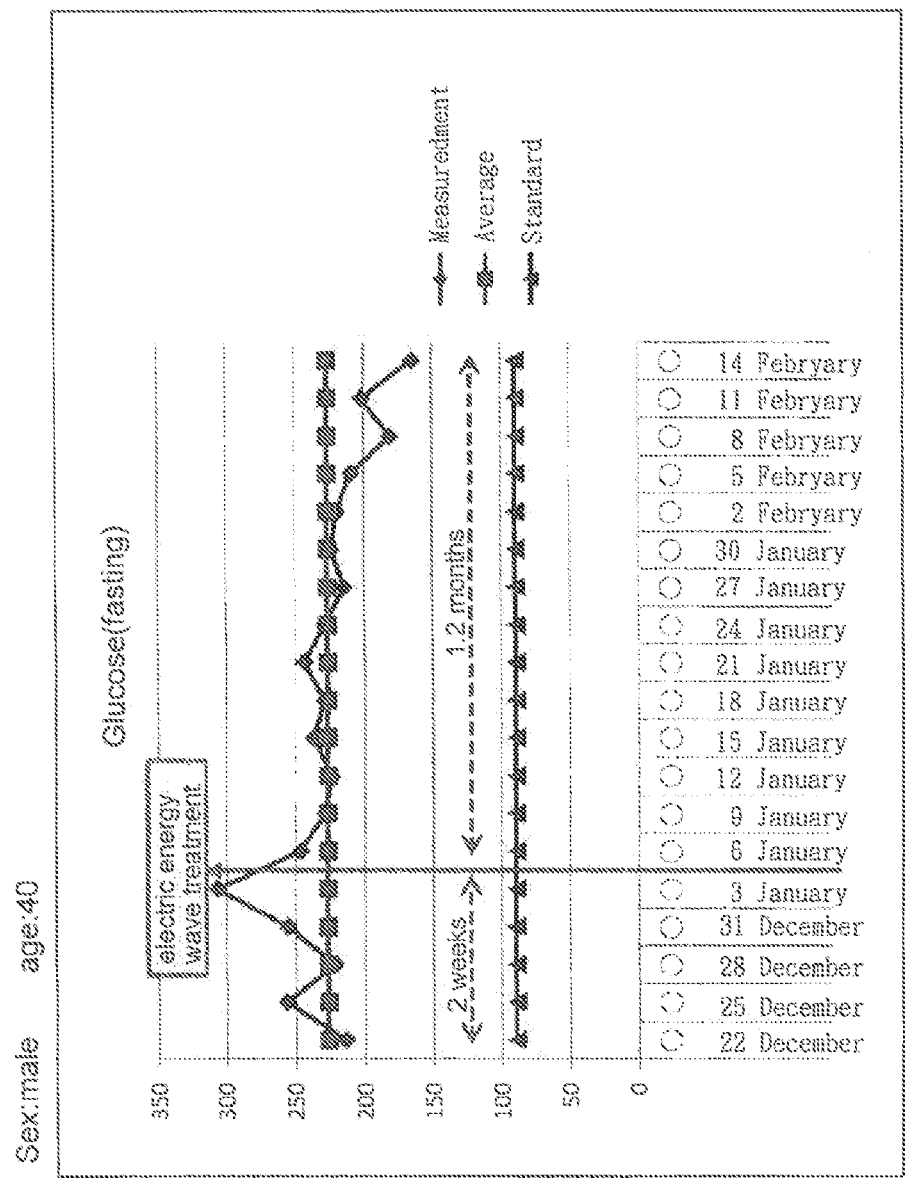
FIG. 7 is a schematic view showing the clinical experiment data of blood sugar of the present invention.
Figure 8:
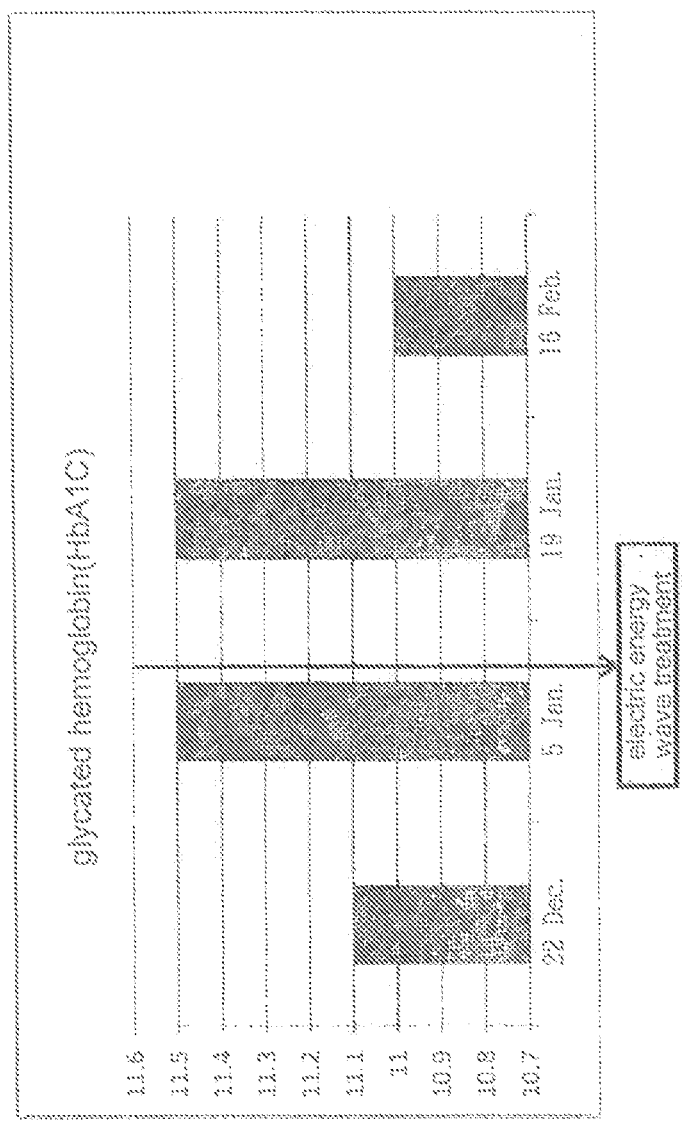
FIG. 8 is a schematic view showing the clinical experiment data of glycated hemoglobin of the present invention.

In an experiment as shown in FIG. 7, a 40-year-old male diabetic patient took a clinical experiment of morning fasting. The graph of FIG. 7 shows that the blood sugar value fluctuates vigorously with a range of 250~310 if the patient has not taken the electric energy wave treatment according to the present invention for two weeks. The blood sugar value tends to become stable within a month after the patient has taken the electric energy wave treatment continuously for approximately 1.2 months. The blood sugar value not longer rise severely, but its starts dropping rapidly. Therefore, the present invention can reduce or eliminate the blood sugar factor of diabetes. In an experiment as shown in FIG. 8, a 40-year-old male diabetic took a clinical experiment of glycated hemoglobin, FIG. 8 shows that after the electric energy wave treatment is taken, the glycated hemoglobin drops slowly, since it requires at least three months before the glycated hemoglobin has a chance to be changed, primarily because the life cycle of hemoglobin is approximately 3 months. Therefore, this experiment shows that the present invention can lower the level of glycated hemoglobin.

Figure 9:
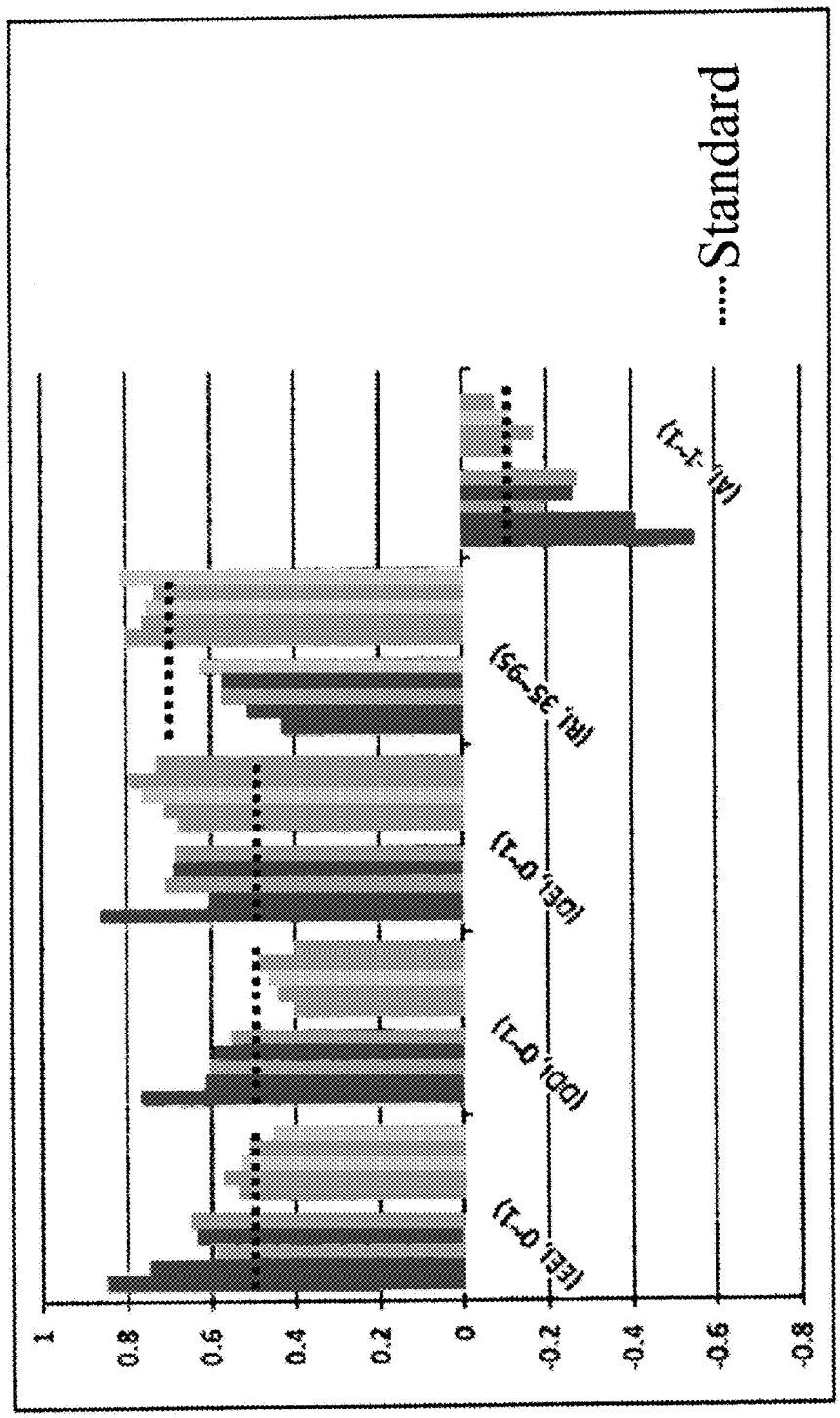
FIG. 9 shows the statistics of pulse measurements of the present invention.
Figure 10:
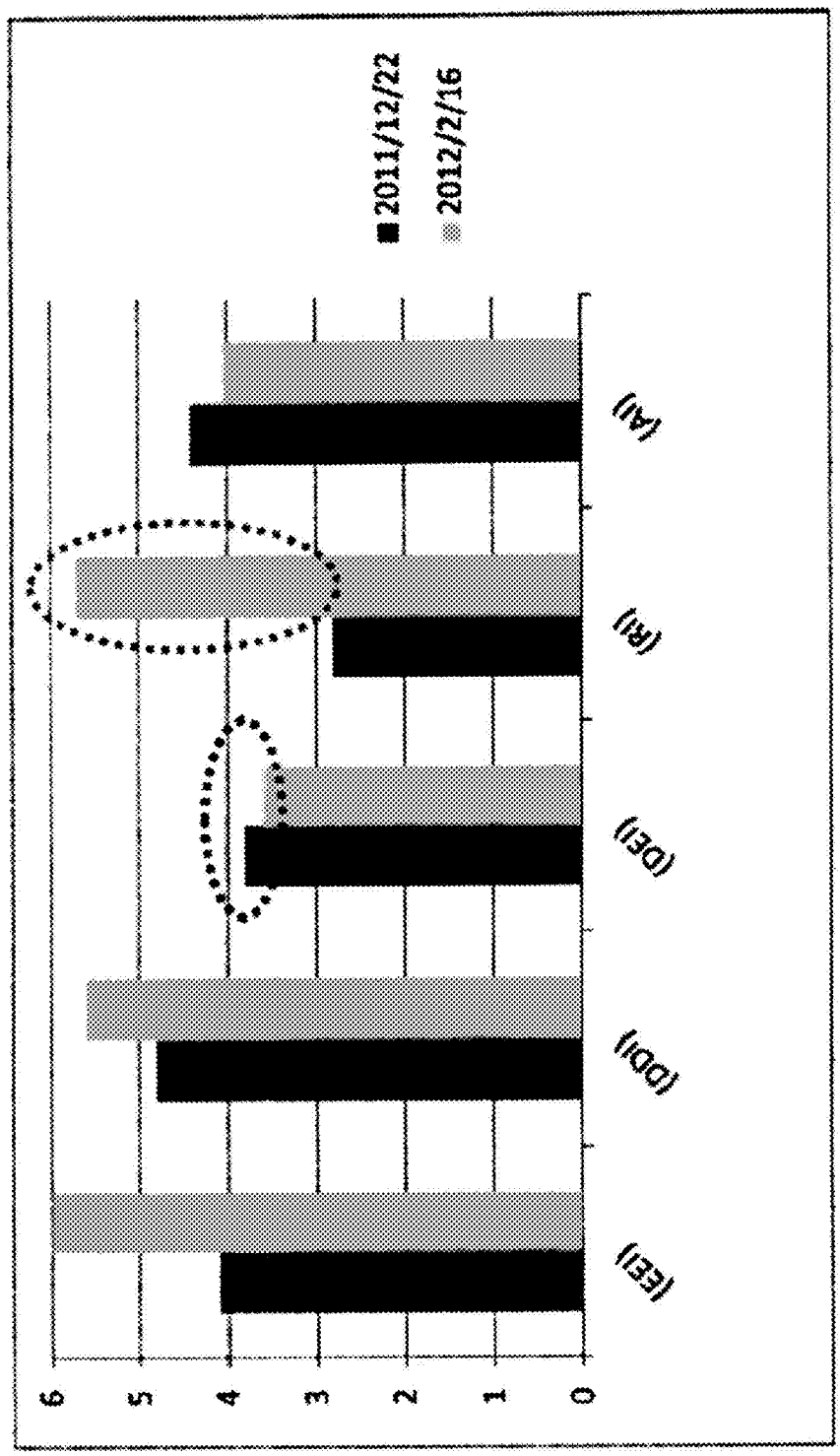
FIG. 10 shows the difference of values before and after using electric energy waves by simple classification and comparison in accordance with the present invention (The best: 6 and the worst: 1).

In FIGS. 9 and 10, experiment results show that the present invention lowers the value of blood sugar and the level of glycated hemoglobin (HbA1C). After a patient has used the electric energy wave formulation according to the present invention for a month, the pulses of five fingers of the patient's right hand are compared, data of the dicrotic elastic index tend to be standard. The Dicrotic Elastic Index (DEI) shows not much difference with blood stasis (AI), but the actual values shown in FIG. 9 indicate that the blood stasis has significant improvement, and Ejection elastic index (EEI), Dicrotic Dilation Index (DDI) and Reflection Index (RI) are improved significantly.

IV. Conclusion

With the aforementioned technical characteristics, the present invention can use the electric energy waves of frequency modulation as a formulation to cure diabetes, and clinical experiments show that the electric energy wave controlled and generated according to the frequency modulation can reduce or eliminate the high blood sugar factor of diabetes effectively, and lower the blood sugar value and glycated hemoglobin level, so as to promote insulin secretion and reduce insulin resistance. In addition, the invention also enhances arterial elasticity to improve patients' physical health.

While we have shown and described the embodiment in accordance with the present invention, it should be clear to those skilled in the art that further embodiments may be made without departing from the scope of the present invention.

What is claimed is:

1. A system for relieving high blood sugar factor of diabetes, comprising an electric energy wave generator having a frequency effect level control mode for controlling and generating an electric energy wave, and the frequency effect level control mode including a control of at least one single frequency effect period and a control of at least one multi-frequency modulation effect period, and the electric energy wave generator controlling and emitting at least one single-frequency electric energy wave to a diabetic patient's body according to the frequency effect level control mode in the at least one single frequency effect period and controlling and emitting a multi-frequency electric energy wave in the at least one multi-frequency modulation effect period, and the at least one single-frequency electric energy wave and the at least one multi-frequency electric energy being used to reduce or eliminate a high blood sugar factor of diabetes of the human body, the at least one multi-frequency modulation effect period being selected from a group consisting of a sweep decreasing effect period, a sweep increasing effect period and a spread contract effect period, and the electric energy wave generator controls and emits the multi-frequency electric energy wave to have a frequency decreasing distribution in a predetermined bandwidth in the sweep decreasing effect period, controls and emits the multi-frequency electric energy wave to have a frequency increasing distribution in a predetermined bandwidth in the sweep increasing effect period, and controls and emits the multi-frequency electric energy wave to have an increasing frequency and a decreasing frequency alternately in a predetermined bandwidth in the spread contract effect period.

2. The system for relieving high blood sugar factor of diabetes as claimed in claim 1, wherein the electric energy wave generator comprises an operating interface, a controlling and driving unit, a database for storing spectral data of the electric energy wave and an electric energy wave transmitting unit, and the operating interface is provided for an user to operate to turn on or off the electric energy wave generator, and the controlling and driving unit is triggered by the operating interface to read the spectral data stored in the database and output a driving instruction signal for controlling a connection or disconnection of the electric energy wave transmitting unit, so that the electric energy wave transmitting unit emits the electric energy wave corresponsive to the spectral data.

3. A method for relieving high blood sugar factor of diabetes, comprising the steps of: providing an electric energy wave generator, having a frequency effect level control mode, wherein the frequency effect level control mode includes a control of at least one single frequency effect period and a control of at least one multi-frequency modulation effect period; turning on the electric energy wave generator to control and emit at least one single-frequency electric energy wave and at least one multi-frequency electric energy wave to a diabetic patient's body according to the frequency effect level control mode in the at least one single frequency effect period and in the at least one multi-frequency modulation effect period respectively; and using the at least one single-frequency electric energy wave and the at least one multi-frequency electric energy wave to reduce or eliminate a high blood sugar factor of the diabetic patient's body, the at least one multi-frequency modulation effect period is selected from a group consisting of a sweep decreasing effect period, a sweep increasing effect period and a spread contract effect period, and the electric energy wave generator controls and emits the multi-frequency electric energy wave to have a frequency decreasing distribution in a predetermined bandwidth in the sweep decreasing effect period, controls and emits the multi-frequency electric energy wave to have a frequency increasing distribution in a predetermined bandwidth in the sweep increasing effect period, and controls and emits the multi-frequency electric energy wave to have an increasing frequency and a decreasing frequency alternately in a predetermined bandwidth in the spread contract effect period.

4. The method for relieving high blood sugar factor of diabetes as claimed in claim 3, wherein the at least one single-frequency electric energy wave and the at least one multi-frequency electric energy waves have a rectangular waveform respectively, and have an emittance of 70% in each cycle.

5. The method for relieving high blood sugar factor of diabetes as claimed in claim 3, wherein a time of the at least one single frequency effect period and a time of the at least one multi-frequency modulation effect period are 42.39% and 57.61% of a total time of the at least one single frequency effect period and the at least one multi-frequency modulation effect period respectively.

6. The method for relieving high blood sugar factor of diabetes as claimed in claim 3, wherein the at least one single frequency effect period is multiple, and the single-frequency electric energy wave of each single frequency effect period has a different frequency, and the frequencies in the single frequency effect periods are decreasing from the start to the end of the single frequency effect periods.

7. The method for relieving high blood sugar factor of diabetes as claimed in claim 3, wherein the at least one multi-frequency modulation effect periods is multiple including the sweep decreasing effect period, the sweep increasing effect period and the spread contract effect period; a time of the sweep decreasing effect period, a time of the sweep increasing effect period and a time of the spread contract effect period in the plurality of multi-frequency modulation effect periods are 30.23%, 43.91% and 25.86% of a total time of the multi-frequency modulation effect periods respectively.

8. The method for relieving high blood sugar factor of diabetes as claimed in claim 3, wherein every two adjacent frequencies controlled in the sweep decreasing effect period have a difference of 1 Hz, and every two adjacent frequencies controlled in the sweep increasing effect period have a difference of 1 Hz, and every two adjacent increasing frequency values and every two adjacent decreasing frequency values controlled in the spread contract effect period have a difference of 1 Hz, and the predetermined bandwidth controlled in the sweep decreasing effect period is 1~3 Hz, and the predetermined bandwidth controlled in the sweep increasing effect period is 2~9 Hz, and the predetermined bandwidth controlled in the spread contract effect period is 5~9 Hz.

9. The method for relieving high blood sugar factor of diabetes as claimed in claim 8, wherein there are 2~4 output frequencies in the sweep decreasing effect period 3~10 output frequencies in the sweep increasing effect period, and 11~19 output frequencies in the spread contract effect period.

* * * * *